United States Patent
Wang et al.

(10) Patent No.: US 7,762,986 B2
(45) Date of Patent: Jul. 27, 2010

(54) SAFETY CONTAINER FOR A SCALP VEIN NEEDLE

(75) Inventors: Shih-Chun Wang, Chia-Yi (TW); Kiwi Yuan, Taipei (TW); Jia-Ming Chang, Banciao (TW)

(73) Assignee: Biotop Holding Co., Ltd., Grand Cayman (KY)

( * ) Notice: Subject to any disclaimer, the term of this patent is extended or adjusted under 35 U.S.C. 154(b) by 1289 days.

(21) Appl. No.: 11/272,879

(22) Filed: Nov. 15, 2005

(65) Prior Publication Data

US 2007/0112307 A1 May 17, 2007

(51) Int. Cl.
*A61M 5/00* (2006.01)
*A61M 5/32* (2006.01)

(52) U.S. Cl. .............. 604/110; 604/180; 604/174

(58) Field of Classification Search ............. 604/110, 604/171, 174, 177, 180, 263
See application file for complete search history.

(56) References Cited

U.S. PATENT DOCUMENTS

| | | | | |
|---|---|---|---|---|
| 3,640,275 A | * | 2/1972 | Burke et al. | 604/177 |
| 4,846,811 A | | 7/1989 | Vanderhoof | |
| 4,898,587 A | * | 2/1990 | Mera | 604/174 |
| 4,927,415 A | | 5/1990 | Brodsky | |
| 4,950,252 A | | 8/1990 | Luther et al. | |
| 5,108,376 A | | 4/1992 | Bonaldo | |
| 5,112,311 A | * | 5/1992 | Utterberg et al. | 604/177 |
| 5,120,320 A | * | 6/1992 | Fayngold | 604/177 |
| 5,137,515 A | | 8/1992 | Hogan | |
| 5,169,391 A | | 12/1992 | Vogel | |
| 5,195,974 A | | 3/1993 | Hardy | |
| 5,267,975 A | | 12/1993 | Brodsky | |
| 5,413,562 A | * | 5/1995 | Swauger | 604/179 |
| 5,433,703 A | | 7/1995 | Utterberg et al. | |
| 5,456,668 A | | 10/1995 | Ogle, II | |
| 5,498,241 A | | 3/1996 | Fabozzi | |
| 5,693,032 A | * | 12/1997 | Bierman | 604/180 |
| 5,800,400 A | | 9/1998 | Hogan | |
| 5,800,402 A | * | 9/1998 | Bierman | 604/180 |
| 5,810,781 A | * | 9/1998 | Bierman | 604/174 |
| 5,931,815 A | | 8/1999 | Liu | |
| 5,947,931 A | * | 9/1999 | Bierman | 604/180 |
| 5,951,522 A | | 9/1999 | Rosato et al. | |
| 5,951,525 A | | 9/1999 | Thorne et al. | |
| 6,001,083 A | | 12/1999 | Wilner | |
| 6,117,163 A | * | 9/2000 | Bierman | 606/232 |
| 6,132,398 A | * | 10/2000 | Bierman | 604/174 |
| 6,270,480 B1 | * | 8/2001 | Dorr et al. | 604/158 |
| 6,491,664 B2 | * | 12/2002 | Bierman | 604/180 |
| 6,582,403 B1 | * | 6/2003 | Bierman et al. | 604/174 |
| 6,736,798 B2 | * | 5/2004 | Ohkubo et al. | 604/177 |
| 6,783,002 B1 | | 8/2004 | Pavlo | |
| 6,824,527 B2 | | 11/2004 | Gollobin | |

(Continued)

*Primary Examiner*—Nicholas D Lucchesi
*Assistant Examiner*—Victoria P Campbell
(74) *Attorney, Agent, or Firm*—Rabin & Berdo, P.C.

(57) ABSTRACT

A safety container for a scalp vein needle has a base, a cap and a covering sheet. The base has an inlet, an outlet and a recess communicating with the inlet and the outlet. The cap connects to and selectively covers the base and has a corresponding inlet, a corresponding outlet, a corresponding recess and a through hole aligning with the outlet. The covering sheet connects to and selectively covers the cap and has two stops selectively extending into the through hole in the cap. The scalp vein needle assembly has a feeding tube, a flange and a scalp vein needle. The feeding tube is mounted in the recesses and is selectively held by the stops on the cap or is slidable in the recesses.

4 Claims, 7 Drawing Sheets

U.S. PATENT DOCUMENTS

| | | | |
|---|---|---|---|
| 6,972,003 B2* | 12/2005 | Bierman et al. | 604/180 |
| 7,367,962 B2* | 5/2008 | Lim et al. | 604/198 |
| 2002/0026152 A1* | 2/2002 | Bierman | 604/174 |
| 2003/0216694 A1* | 11/2003 | Tollini | 604/174 |
| 2003/0229313 A1* | 12/2003 | Bierman | 604/174 |
| 2004/0019334 A1* | 1/2004 | Ohkubo et al. | 604/263 |
| 2007/0173765 A2* | 7/2007 | Bierman et al. | 604/174 |
| 2008/0125718 A1* | 5/2008 | Tsuchiya et al. | 604/174 |

* cited by examiner

SAFETY CONTAINER FOR A SCALP VEIN NEEDLE

BACKGROUND OF THE INVENTION

1. Field of the Invention

The present invention relates to a container for a scalp vein needle, especially to a safety container for a scalp vein needle.

2. Description of the Prior Arts

Scalp vein needles are used to inject medicinal liquid into thin veins such as veins in a person's scalp and baby's veins. To keep the needles from stabbing the user when the needles are removed from the veins, the conventional scalp vein needle apparatus comprises a scalp vein needle, a container and a retracting device. The scalp vein needle is mounted slidable in the container and connects to the retracting device. The retracting device retracts the scalp vein needle into the container to keep the needle from stabbing the user when the needle is removed from a vein. To keep the scalp vein needle securely in the vein, a piece of adhesive tape is stuck on the scalp vein needle and a patient's skin. When the scalp vein needle is to be removed, the adhesive tape has to be removed before the retracting device can retract the scalp vein needle into the container. However, the scalp vein needle is easily pulled out of the skin when the adhesive tape is removed. A scalp vein needle that pulls out of a patient's skin without being retracted by the retracting device easily stabs the user. In addition to being expensive, the retracting device is complicated.

To overcome the shortcomings, the present invention provides a safety receptacle for a scalp vein needle to mitigate or obviate the aforementioned problems.

SUMMARY OF THE INVENTION

The main objective of the present invention is to provide a safety container with a simple structure for a scalp vein needle. The safety container for a scalp vein needle has a base, a cap and a covering sheet. The base has an inlet, an outlet and a recess communicating with the inlet and the outlet. The cap connects to and selectively covers the base and has a corresponding inlet, a corresponding outlet, a corresponding recess and a through hole aligning with the outlet. The covering sheet connects to and selectively covers the cap and has two stops selectively extending into the through hole in the cap. The scalp vein needle assembly has a feeding tube, a flange and a scalp vein needle. The feeding tube is mounted in the recesses and is selectively held by the stops on the cap or is slidable in the recesses.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
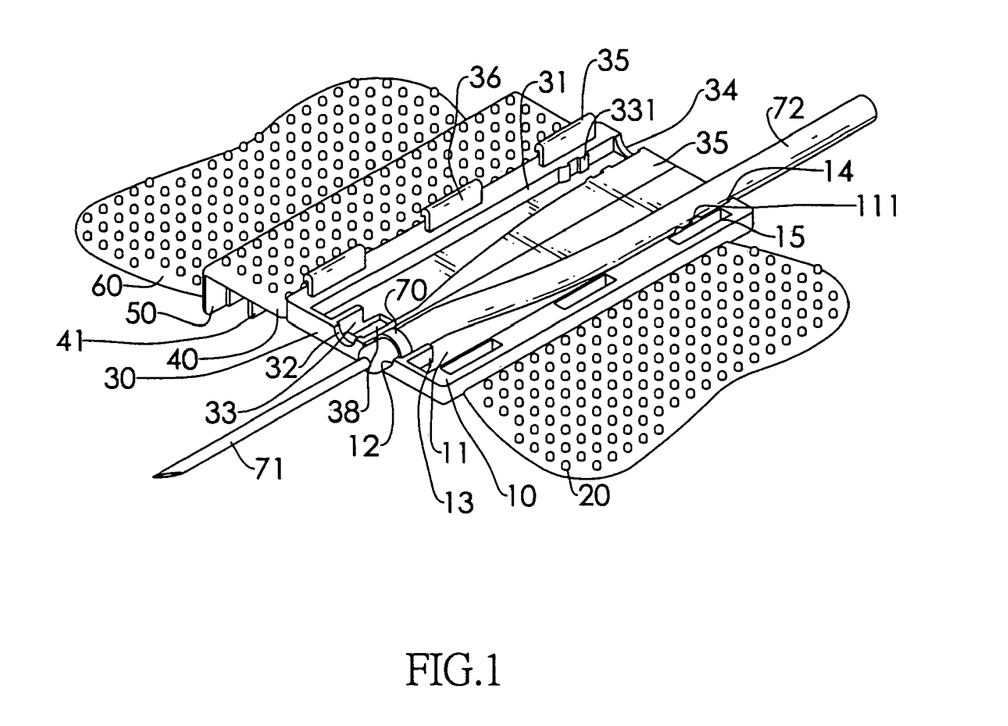
FIG. 1 is a perspective view of a safety container for a scalp vein needle in accordance with the present invention as part of a scalp vein needle assembly.

With reference to FIG. 1, a safety container for a scalp vein needle in accordance with the present invention comprises a base (10), a first wing (20), a cap (30), a covering sheet (40), an adapting sheet (50) and a second wing (60).

The base (10) has a proximal side, a distal side, an input end, an output end, an outlet (12), an inlet (14), a recess (11), multiple keyholes (15), an optional limit (13) and an optional protrusion (111). The proximal side has an inside edge and an outside edge. The distal side has an inside edge and an outside edge. The outlet (12) is formed through the output end. The inlet (14) is formed through the input end. The recess (11) is formed in the base (10), communicates with the outlet (12) and the inlet (11) and has an output end and an input end. The recess (11) may be inclined from the input end to the output end, and the output end of the recess (11) may be wider than the input end of the recess (11). The keyholes (15) are formed in the base (10) near the distal side of the base (10). The limit (13) is formed in the recess (11) on the output end of the recess (11) adjacent to the outlet (12) of the base (10). The protrusion (111) is formed in the recess (11) adjacent to the input end of the recess (11).

The first wing (20) is attached to the outside edge of the distal side of the base (10).

Figure 2:
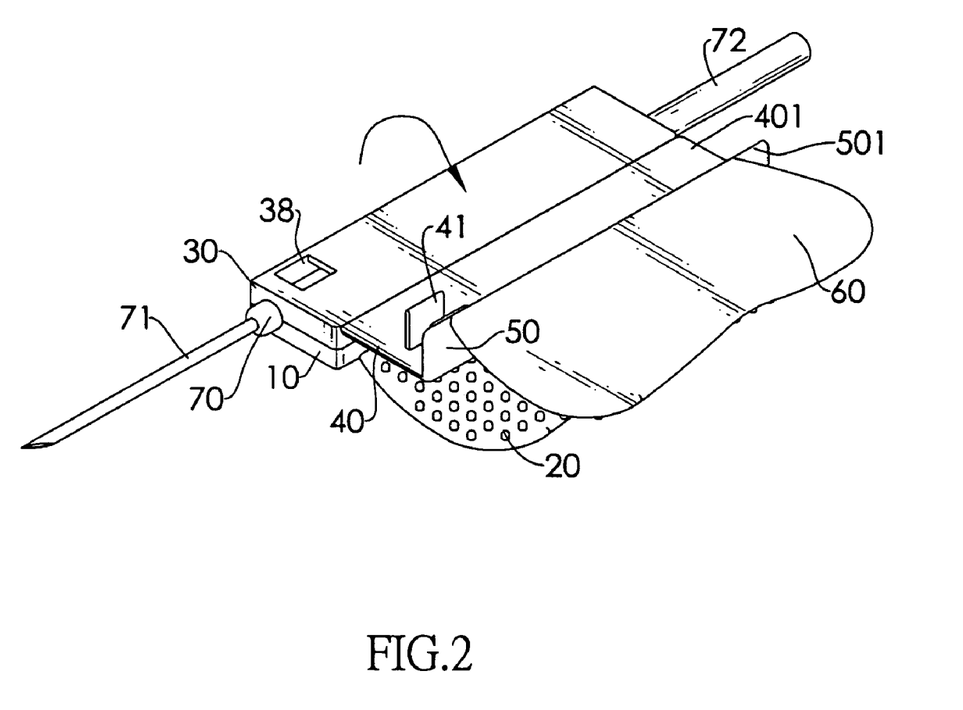
FIG. 2 is an operational perspective view of the scalp vein needle assembly in FIG. 1.

With further reference to FIG. 2, the cap (30) connects to and selectively covers the base (10) and has a proximal side, a distal side, an input end, an output end, an outlet (32), an inlet (34), a recess (31), multiple keys (35), a through hole (38), an optional limit (33) and an optional protrusion (331). The proximal side has an inside edge and an outside edge. The inside edge of the proximal side of the cap (30) connects to the inside edge of the proximal side of the base (10). The distal side has an inside edge and an outside edge. The outlet (32) is formed through the output end of the cap (30) and corresponds to the outlet (12) in the base (10). The inlet (34) is formed through the input end of the cap (30) and corresponds to the inlet (14) in the base (10). The recess (31) is formed in the cap (30), communicates with the outlet (32) and the inlet (34) in the cap (30) and corresponds to the recess (11) in the base (10). The keys (35) are formed on the cap (30) and are selectively held in the keyholes (15) to hold the cap (30) closed on the base (10). The through hole (38) is formed through the cap (30) near the outlet (32) in the cap (30), communicates with the recess (31) in the cap (30) and aligns with the outlet (32) in the cap (30). The limit (33) is formed in the recess (31) on the output end of the cap (30) and corresponds to the limit (13) in the base (10). The protrusion (331) is formed in the recess (31) near the input end of the cap (30) and corresponds to the protrusion (111) on the base (10).

Figure 3:
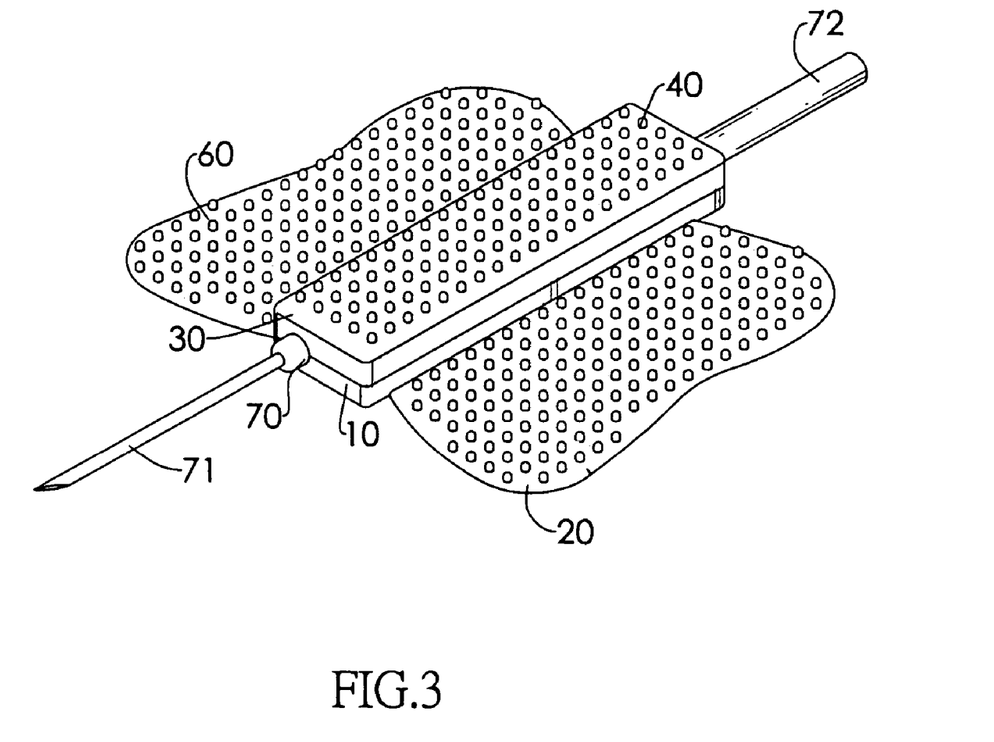
FIG. 3 is another operational perspective view of the scalp vein needle assembly in FIG. 1.

With further reference to FIG. 3, the covering sheet (40) connects to and selectively covers the cap (30) and has a first side, a second side, an inside surface (401) and two stops (41). The first side of the covering sheet (40) connects to the outside edge of the distal side of the cap (30). The stops (41) are formed on the inside surface (401) of the covering sheet (40) and corresponds to and selectively extend into the through hole (38) in the cap (30).

The adapting sheet (50) is formed on the inside surface on the second side of the covering sheet (40) and has a distal edge (501).

The second wing (60) is attached to the distal edge (501) of the adapting sheet (50).

The scalp vein needle assembly is mounted in the safety container and comprises a feeding tube (72), a flange (70) and a scalp vein needle (71). The feeding tube (72) extends into the recess (11) in the base (10) through the inlet (14) in the base (10), extends out through the outlet (12) in the base (10) and has an end. The flange (70) is mounted on the feeding tube (72) and abuts the output end of the recess (11) in the base (10). The scalp vein needle (71) is mounted in the end of the feeding tube (70).

The cap (30) covers the base (10), and the feeding tube (72) is mounted in the inlets (13, 32) and the outlets (14, 34) and between the protrusions (111, 331).

Figure 4:
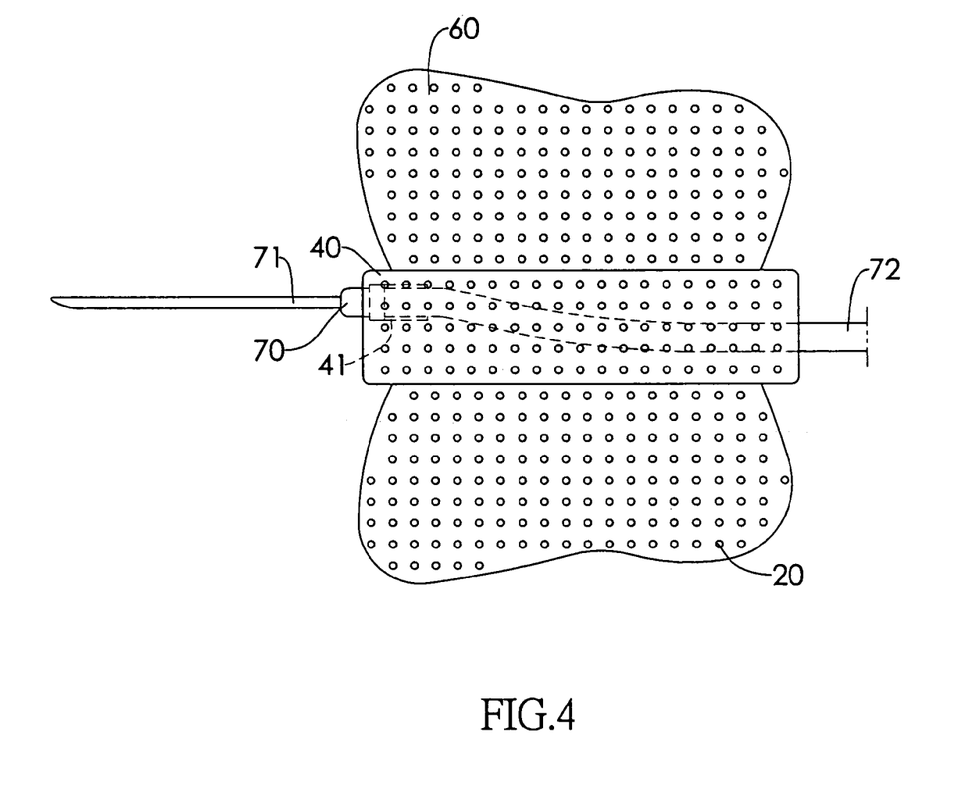
FIG. 4 is an operational top view of the scalp vein needle assembly in FIG. 3.

With further reference to FIG. 4, the covering sheet (40) covers the cap (30), and the stops (41) extend into the through hole (38) in the cap (30) and hold the feeding tube (72) to keep the feeding tube (72) form sliding out of the safety container.

After the scalp vein needle (71) is inserted into a vein, adhesive tape is stuck on the first and second wings (20, 60), the covering sheet (40) and a patient's skin to hold the scalp vein needle (71) in the vein.

Figure 5:
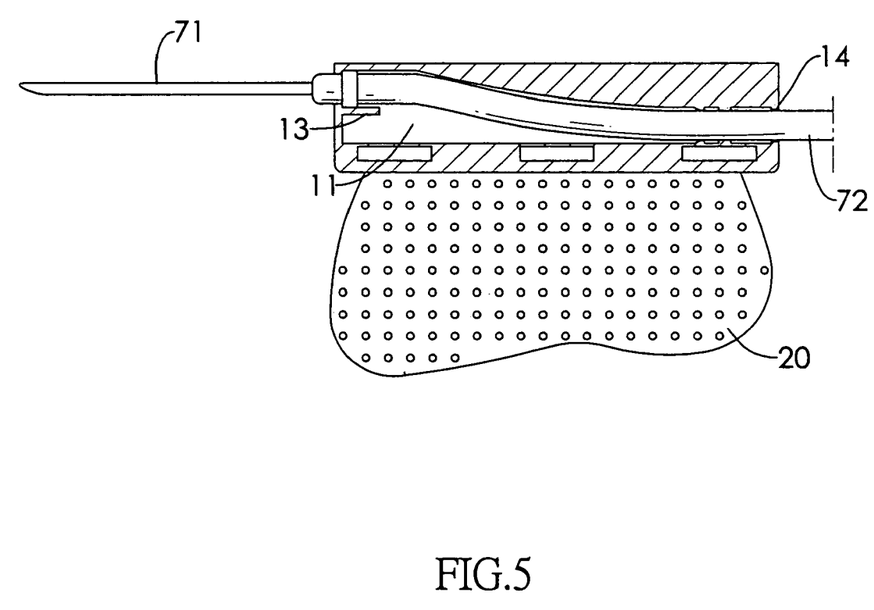
FIG. 5 is an operational top view in partial section of the scalp vein needle assembly in FIG. 3.
Figure 6:
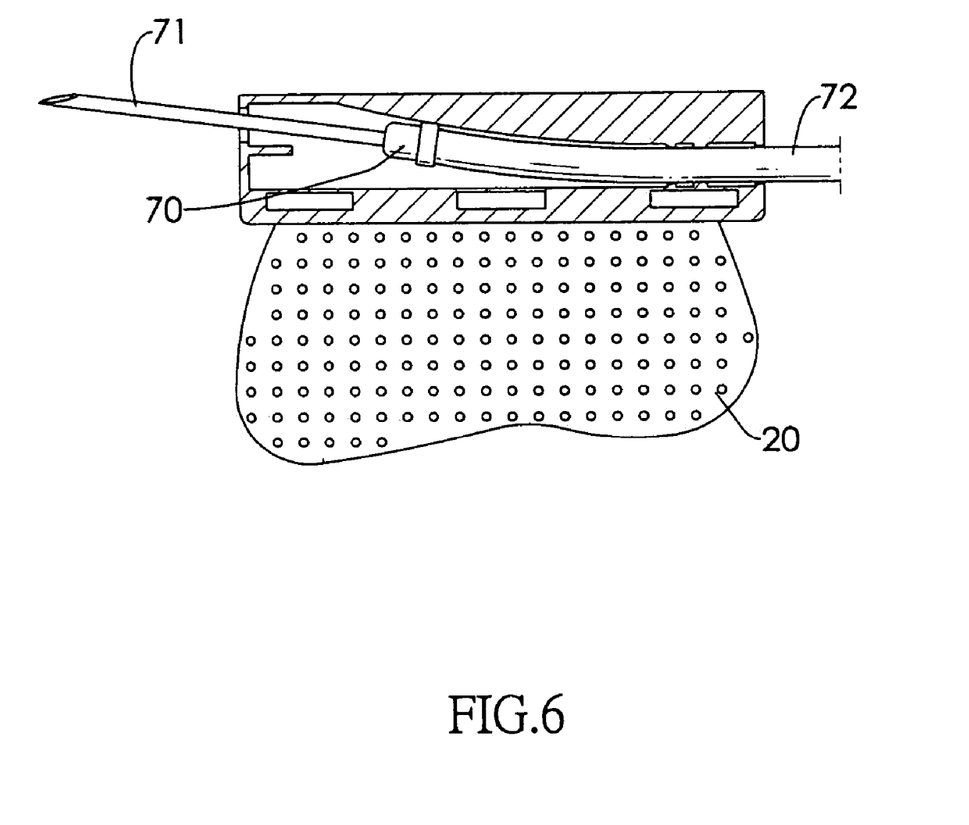
FIG. 6 is an operational top view in partial section of the scalp vein needle assembly in FIG. 3 when the scalp vein needle is being retracted.
Figure 7:
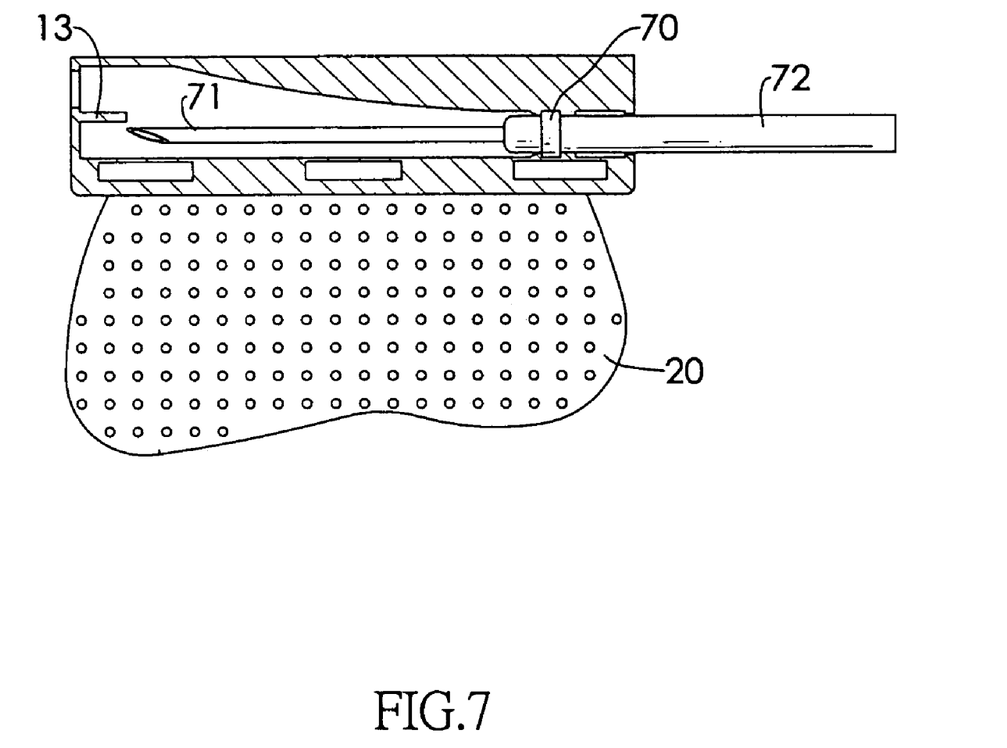
FIG. 7 is an operational top view in partial section of the scalp vein needle assembly in FIG. 3 when the scalp vein needle is retracted.

With further reference to FIGS. 5, 6 and 7, the scalp vein needle (71) is removed from a patient's vein by removing the adhesive tape attached to the second wing (60) from the patient's skin and pivoting the second wing (60) and the covering sheet (40) toward the first wing (20). Pivoting the second wing (60) and the covering sheet (40) toward the first wing (20) extracts the stops (41) from the through hole (38) in the cap (30) and releases the feeding tube (72). Then the feeding tube (72) is pulled from the inlets (14, 34) to retract the scalp vein needle (71) from the vein into the safety container. After the scalp vein needle (71) is completely retracted into the container, the limits (13, 33) keep the scalp vein needle (71) from accidentally protruding from the outlets (12, 32).

As described, the safety container for a scalp vein needle has a number of advantages over the conventional safety container for a scalp vein needle. First, the safety container for a scalp vein needle has a simple, one-piece structure that makes manufacturing the safety container simple and less expensive. Second, the stops (41) on the covering sheet (40) selectively lock the feeding tube (72) in an extended position in the safety container or release the feeding tube (72) so the scalp vein needle (71) can be retracted into the safety container. Third, the safety container does not have to be released from the patent's skin to draw the scalp vein needle (71) out of the patient's vein. Therefore, having the scalp vein needle (71) pull out of the skin when the adhesive tape is removed to extract the scalp vein needle (71) is completely avoided. The scalp vein needle (71) is retracted into the safety container with the container still taped to the patient's skin. Consequently, a user being stabbed when extracting the scalp vein needle (71) is virtually impossible.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A safety container for a scalp vein needle comprising
   a base having
      a proximal side having an inside edge and an outside edge;
      a distal side having an inside edge and an outside edge;
      an input end;
      an output end;
      an outlet formed through the output end;
      an inlet formed through the input end;
      a recess formed in the base, communicating with the outlet and the inlet and having an output end and an input end; and
      multiple keyholes formed in the base near the distal side of the base;
   a first wing attached to the outside edge of the distal side of the base;
   a cap connecting to and selectively covering the base and having
      a proximal side having
         an inside edge connecting to the inside edge of the proximal side of the base; and
         an outside edge;
      a distal side having an inside edge and an outside edge;
      an input end;
      an output end;
      an outlet formed through the output end of the cap and corresponding to the outlet in the base;
      an inlet formed through the input end of the cap and corresponding to the inlet in the base;
      a recess formed in the cap, communicating with the outlet and the inlet in the cap and corresponding to the recess in the base;
      multiple keys formed on the cap and selectively held in the keyholes; and
      a through hole formed through the cap near the outlet in the cap, communicating with the recess in the cap and aligning with the outlet in the cap;
   a covering sheet connecting to and selectively covering the cap and having
      a first side connecting to the outside edge of the distal side of the cap;
      a second side;
      an inside surface; and
      two stops formed on the inside surface of the covering sheet and corresponding to and selectively extending into the through hole in the cap;
   an adapting sheet formed on the inside surface on the second side of the covering sheet and having a distal edge; and
   a second wing attached to the distal edge of the adapting sheet.

2. The safety container as claimed in claim 1, wherein
   the recess in the base is inclined from the input end to the output end; and
   the output end of the recess of the base is wider than the input end of the recess in the base;
   the base has a limit formed in the recess on the output end of the recess adjacent to the outlet of the base; and
   the cap has a limit formed in the recess on the output end of the cap and corresponding to the limit in the base.

3. The safety container as claimed in claim 1, wherein
   the base has a protrusion formed in the recess of the base adjacent to the input end of the recess of the base; and
   the cap has a protrusion formed in the recess of the cap near the input end of the cap and corresponding to the protrusion on the base.

4. The safety container as claimed in claim 2, wherein
   the base has a protrusion formed in the recess of the base adjacent to the input end of the recess of the base; and
   the cap has a protrusion formed in the recess of the cap near the input end of the cap and corresponding to the protrusion on the base.

* * * * *